(12) United States Patent
Gao et al.

(10) Patent No.: US 9,851,753 B2
(45) Date of Patent: Dec. 26, 2017

(54) ELECTRONIC DEVICE AND METHOD FOR CONTROLLING POWER SUPPLY OF ELECTRONIC DEVICE

(71) Applicant: Lenovo (Beijing) Co., Ltd., Beijing (CN)

(72) Inventors: Yan Gao, Beijing (CN); Xiaotian Zhu, Beijing (CN); Sang-ho Lee, Beijing (CN)

(73) Assignee: Lenovo (Beijing) Co., Ltd., Beijing (CN)

( * ) Notice: Subject to any disclaimer, the term of this patent is extended or adjusted under 35 U.S.C. 154(b) by 69 days.

(21) Appl. No.: 14/755,657

(22) Filed: Jun. 30, 2015

(65) Prior Publication Data

US 2016/0192526 A1   Jun. 30, 2016

(30) Foreign Application Priority Data

Dec. 31, 2014   (CN) .......................... 2014 1 0852507
Mar. 9, 2015    (CN) .......................... 2015 1 0103668

(51) Int. Cl.
| | |
|---|---|
| *G06F 1/16*   | (2006.01) |
| *G04G 21/00*  | (2010.01) |
| *G06F 1/26*   | (2006.01) |
| *A61B 5/00*   | (2006.01) |
| *A61B 5/024*  | (2006.01) |
| *A61B 5/11*   | (2006.01) |

(52) U.S. Cl.
CPC .............. *G06F 1/163* (2013.01); *G04G 21/00* (2013.01); *G06F 1/1632* (2013.01); *G06F 1/1654* (2013.01); *G06F 1/263* (2013.01); *A61B 5/02438* (2013.01); *A61B 5/11* (2013.01); *A61B 5/4809* (2013.01); *A61B 5/681* (2013.01)

(58) Field of Classification Search
CPC ....... G06F 1/163; G06F 1/1654; G04G 17/00; G04G 17/08
USPC ..................................................... 361/679.03
See application file for complete search history.

(56) References Cited

U.S. PATENT DOCUMENTS

| | | | | |
|---|---|---|---|---|
| 5,392,261 A    | * | 2/1995  | Hsu ...................... | G04B 37/1413 368/281 |
| 2002/0085455 A1 | * | 7/2002  | Haida ................. | G04B 37/1486 368/281 |
| 2005/0237704 A1 | * | 10/2005 | Ceresoli ................. | G06F 1/163 361/679.03 |
| 2007/0279852 A1 | * | 12/2007 | Daniel ................. | A44C 5/0007 361/679.03 |
| 2008/0043575 A1 | * | 2/2008  | Fasciano .............. | G04G 9/0076 368/13 |
| 2008/0074958 A1 | * | 3/2008  | Moran ............... | G04B 37/1486 368/282 |

(Continued)

*Primary Examiner* — Adrian S Wilson
(74) *Attorney, Agent, or Firm* — Harness, Dickey & Pierce, P.L.C.

(57) ABSTRACT

An electronic device includes a first body and a second body which are detachably connected. The first body includes a frame and a fixing apparatus, and the second body includes a main functional unit. The fixing apparatus is connected to the frame and configured to fix the electronic device to an operation body. When the electronic device is fixed to the operation body via the fixing apparatus, the fixing apparatus and the frame form a ring-shaped space. A method for controlling power supply of the electronic device is also provided.

15 Claims, 7 Drawing Sheets

(56) References Cited

U.S. PATENT DOCUMENTS

| | | | |
|---|---|---|---|
| 2011/0007468 A1* | 1/2011 | Burton | G04F 10/00 361/679.03 |
| 2012/0087216 A1* | 4/2012 | Keung | A44C 5/0084 368/282 |
| 2015/0130666 A1* | 5/2015 | Pan | H02J 7/0045 343/702 |
| 2015/0131216 A1* | 5/2015 | Huang | H02J 7/0045 361/679.03 |

* cited by examiner

ELECTRONIC DEVICE AND METHOD FOR CONTROLLING POWER SUPPLY OF ELECTRONIC DEVICE

This application claims the benefit of priorities to Chinese patent application No. 201410852507.X, titled "POWER SUPPLY CONTROL METHOD AND ELECTRONIC DEVICE", filed with the Chinese State Intellectual Property Office on Dec. 31, 2014 and Chinese patent application No. 201510103668.3, titled "ELECTRONIC DEVICE", filed with the Chinese State Intellectual Property Office on Mar. 9, 2015, the entire disclosures of which are incorporated herein by reference.

FIELD

The present application relates to the field of electronic technique, and particularly to an electronic device and a method for controlling power supply of an electronic device.

BACKGROUND

With the popularity of electronic devices such as smart mobile phones and touch screens, multi-functional smart watches or smart bands having a touch screen are available on the market. The smart watch or smart band includes a display device, and the display device includes at least one display screen. Various kinds of information, such as time, date, temperature, or user's physical status, may be displayed on an interface where the display screen is located. The smart watch or smart band may be worn on a user's wrist or arm by a fixing apparatus, and the fixing apparatus is connected to a frame on which the display device is mounted. The device has the following issue, when the smart watch or smart band has insufficient power and needs to be charged, or when it is required to use the display device separately, it is required to ensure that the smart watch or the smart band can keep working at the meantime, for example, keep displaying the information, such as time, date or the user's physical status, thus the fixing apparatus of the smart watch or smart band has to be fixed to the user's wrist or arm all along.

SUMMARY

An electronic device is provided according to the present application. The electronic device includes a first body and a second body. The first body includes a frame and a fixing apparatus, the fixing apparatus is connected to the frame and configured to fix the electronic device to an operation body. The fixing apparatus and the frame form a ring-shaped space in the case that the electronic device is fixed to the operation body by the fixing apparatus. The second body is detachably connected to the first body, and includes a main functional unit.

A method for controlling power supply of an electronic device is provided, wherein the electronic device includes a first body and a second body detachably connected to the first body, the first body includes a frame, a fixing apparatus, and an auxiliary functional unit having a first power supply unit, the fixing apparatus is connected to the frame and configured to fix the electronic device to an operation body; the fixing apparatus and the frame form a ring-shaped space in the case that the electronic device is fixed to the operation body by the fixing apparatus, the second body includes a main functional unit having a second power supply unit; and the method includes:

detecting whether the second body is detached from the first body, and generating a detection result;

controlling the first power supply unit to supply power to the auxiliary functional unit in the case the detection result indicates that the second body is detached from the first body; and controlling the second power supply unit of the second body to supply power to both the auxiliary functional unit of the first body and the main functional unit of the second body in the case that the detection result indicates that the second body is coupled to the first body.

BRIEF DESCRIPTION OF THE DRAWINGS

For more clearly illustrating embodiments of the present application or the technical solutions in the conventional technology, drawings referred to describe the embodiments or the conventional technology will be briefly described hereinafter. Apparently, the drawings in the following description are only examples of the present application, and for the person skilled in the art, other drawings may be obtained based on the provided drawings without any creative efforts.

DETAILED DESCRIPTION

The technical solutions in the embodiments of the present application will be described clearly and completely hereinafter in conjunction with the drawings in the embodiments of the present application. Apparently, the described embodiments are only a part of the embodiments of the present application, rather than all embodiments. Based on the embodiments in the present application, all of other embodiments, made by the person skilled in the art without any creative efforts, fall into the scope of the present application.

An electronic device is provided according to an embodiment of the present application, which includes a first body and a second body. The first body includes a frame and a fixing apparatus, and the second body includes a main functional unit. The fixing apparatus is connected to the frame, and is configured to fix the electronic device to an operation body. In the case that the electronic device is fixed to the operation body via the fixing apparatus, the fixing apparatus and the frame form a ring-shaped space. The first body and the second body are detachably connected.

In the case that the first body and the second body are connected, the user can read information on the first body and the second body conveniently. When the second body is required to perform other functions such as being charged, or acting as a separate display unit, the user may detach the second body from the first body. Thus the electronic device according to the present application can be operated conveniently and achieve more functions.

The electronic device according to the embodiments of the present application may be a smart watch, a smart band or the like. The main functional unit of the second body may be a display screen of a smart watch or a smart band.

Figure 1:
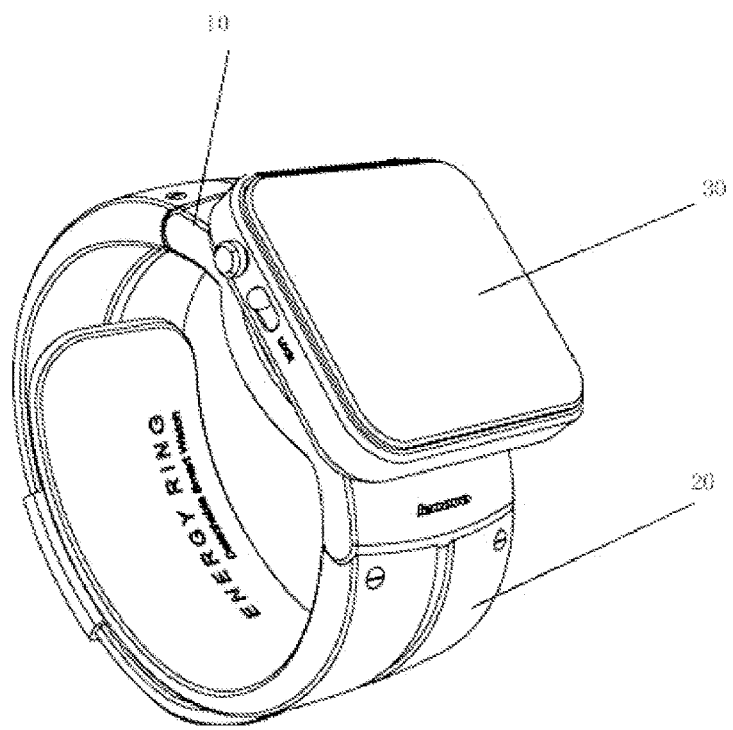
FIG. 1 is a schematic view showing the structure of an embodiment of an electronic device in a first state according to the present application.
Figure 2:
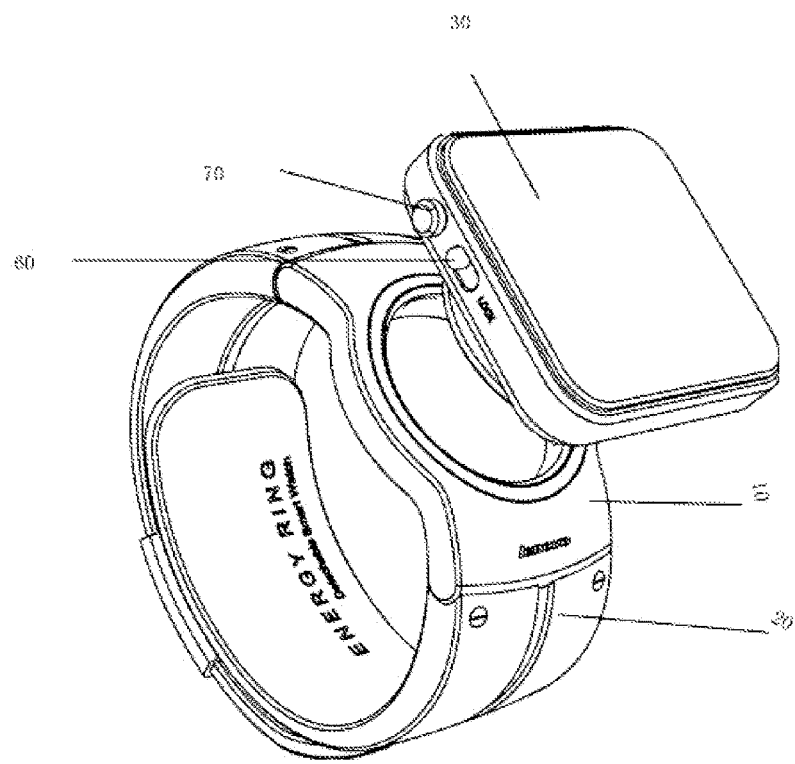
FIG. 2 is a schematic view showing the structure of the embodiment of the electronic device in a second state according to the present application.
Figure 3:
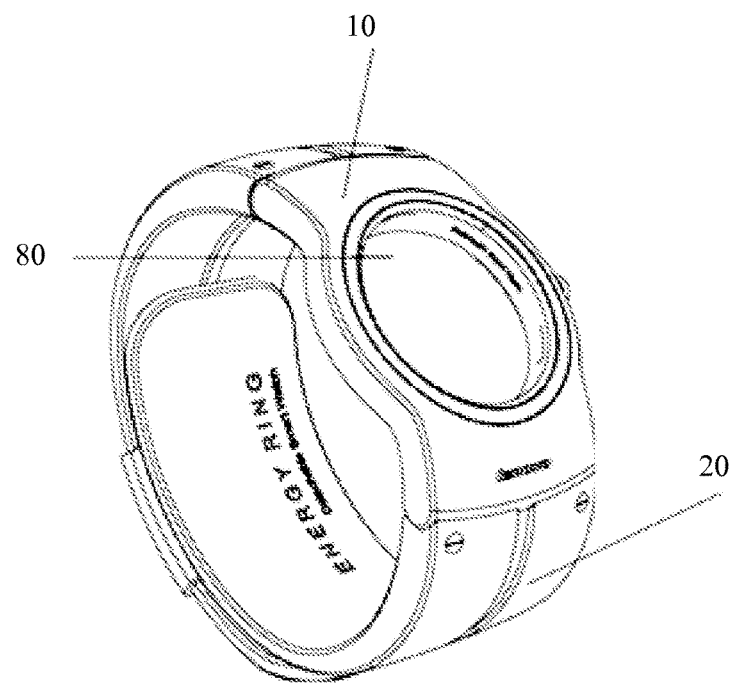
FIG. 3 is a schematic view showing the structure of a first body of the embodiment of the electronic device according to the present application.
Figure 4:
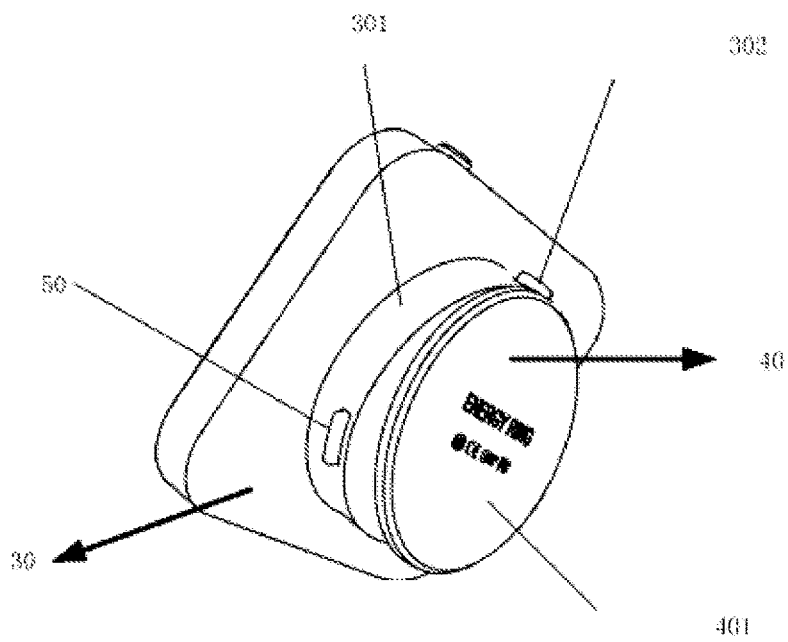
FIG. 4 is a schematic view showing the structure of a second body of the embodiment of the electronic device according to the present application.

Taking the electronic device being a smart watch as an example, FIGS. 1 to 4 are scenario schematic views showing various attitudes of the electronic device in the case that the electronic device is embodied as a smart watch having a detachable screen. FIG. 1 depicts a scenario of the smart watch integrating all functions, in which the main functional unit (for example a display screen) is detachably mounted on the frame, the fixing apparatus is connected to the frame, and the smart watch is fixed to the wrist of a user via the fixing apparatus. FIG. 2 depicts a scenario that the main functional unit (for example, a display screen) is detached from the frame and the fixing apparatus, in which the frame and the fixing apparatus are fixed together, and the frame and the fixing apparatus may also be detached from each other. FIG. 3 depicts a scenario that a through hole of the frame is shown when the main functional unit (for example, a display screen) is detached from the frame. FIG. 4 depicts a scenario showing assembling an elastic component with the main functional unit (for example, a display screen), wherein the elastic component is configured to generate an elastic force to detach the main functional unit (for example, the display screen) from the frame.

It is to be noted that, a triggering button 60 of a locking-unlocking device and a pressing button 70 for assembling and disassembling the functional unit with the frame shown in FIGS. 1 and 2 are optionally, and are not the necessary components of the structure of this electronic device.

Figure 5:
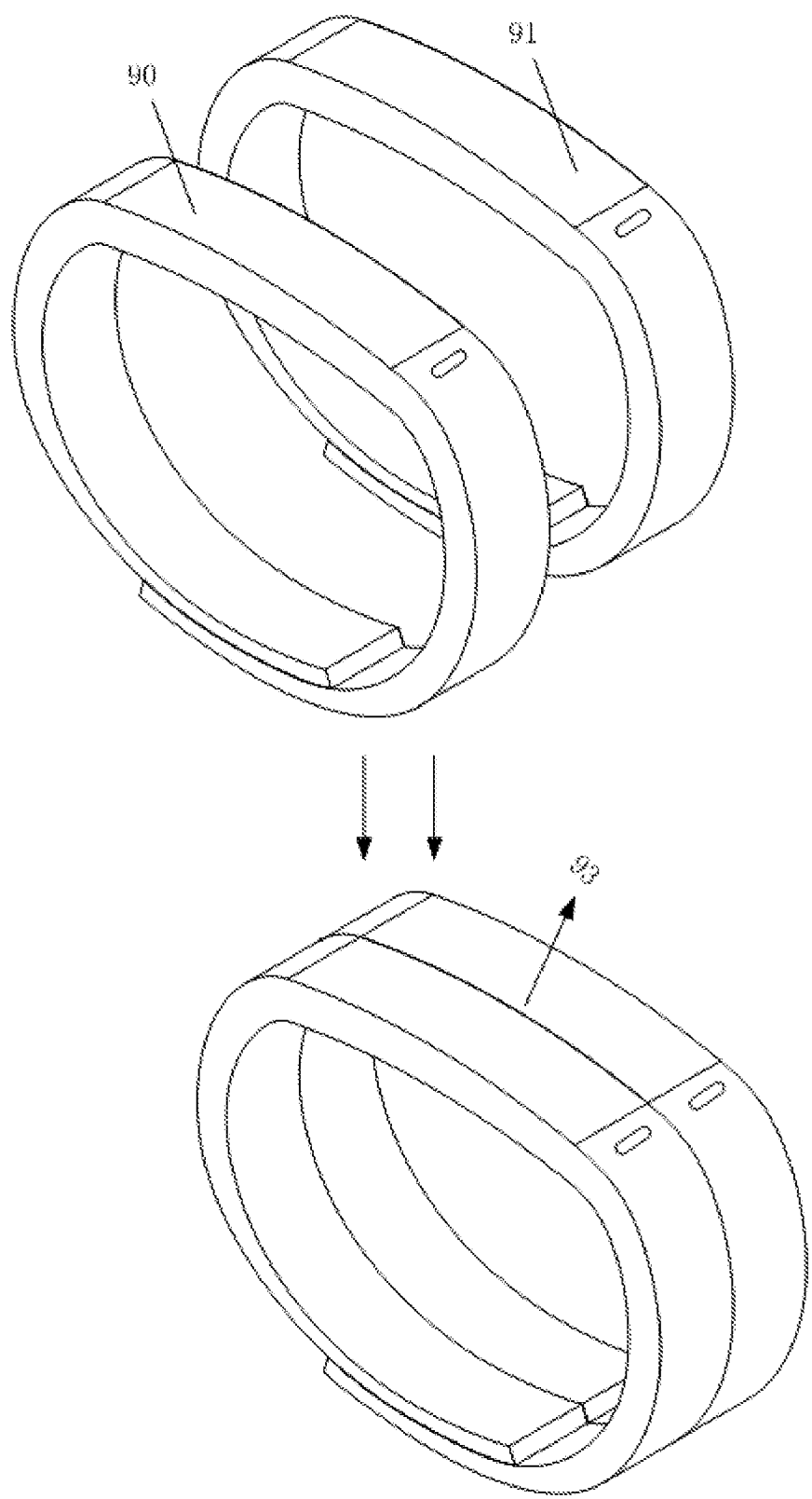
FIG. 5 is a schematic view showing the structure of an embodiment of the electronic device according to the present application.

FIG. 5 shows scenarios that respective screens of two separate smart bands are combined into one integral screen, wherein one smart band can be detached into two separate smart bands or two separate smart bands can be combined into one smart band, and the smart band has the main functional unit (for example, two display screens corresponding to two smart bands respectively) based on the operating principles shown in the scenarios in FIGS. 1 to 4 or other operating principles.

Figure 6:
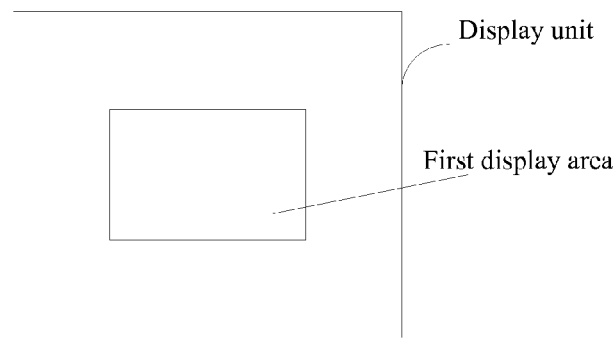
FIG. 6 is a schematic view showing a display module of the embodiment of the electronic device according to the present application.
Figure 7A:
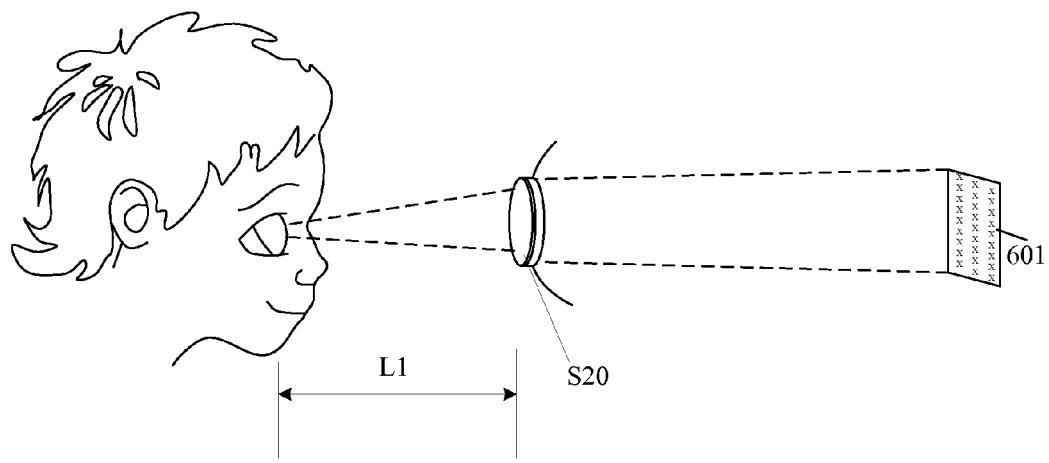
FIGS. 7a and 7b are schematic views showing display modes of the display module in the embodiment of the electronic device according to the present application.
Figure 7B:
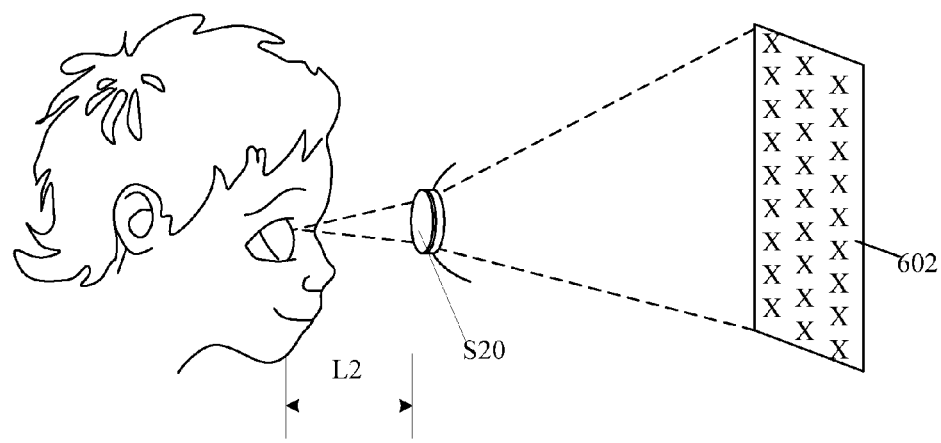

FIGS. 6, 7a and 7b are schematic views showing the display module of the smart watch or smart band according to the embodiments of the electronic device of the present application. FIG. 6 depicts a relationship between a first display area and the display unit in a first display mode in a state that the main functional unit and the frame are assembled. In another scenario corresponding to the relationship in FIG. 6, a relationship between a second display area and the display unit in a second display mode in a state that the main functional unit and the frame are detached, is not depicted and will be described by written description in the following. It is to be noted that, the second display area is larger than the first display area, and the first display area is a partial area of a display unit 152, and the second display area may be the entire area of the display unit 152. FIG. 7a depicts a scenario of display output in the first display mode in the case that the main functional unit and the frame are assembled. FIG. 7b depicts a scenario of display output in the second display mode in the case that the main functional unit and the frame are detached.

First Embodiment of the Electronic Device

The electronic device according to this embodiment of the present application is shown in FIGS. 1 to 4. The electronic device includes a first body and a second body. The first body includes a frame 10 and a fixing apparatus 20, and the second body includes a main functional unit 30. The fixing apparatus 20 is connected to the frame 10, and is configured to fix the electronic device to an operation body, for example, the wrist of a user. In the case that the electronic device is fixed to the operation body via the fixing apparatus 20, the fixing apparatus 20 and the frame 10 form a ring-shaped space. The second body and the first body are detachably connected. The main functional unit 30 of the second body is detachably mounted on the frame 10 of the first body. Here, the main functional unit 30 may be a display screen of a smart watch, and is a detachable screen.

Second Embodiment of the Electronic Device

The electronic device according to this embodiment of the present application is shown in FIGS. 1 to 4. The electronic device includes a first body and a second body. The first body includes a frame 10 and a fixing apparatus 20, and the second body includes a main functional unit 30. The second body further includes an elastic component 40 (as shown in FIG. 4). The fixing apparatus 20 is connected to the frame 10, and is configured to fix the electronic device to the wrist of the user. In the case that the electronic device is fixed to the wrist via the fixing apparatus 20, the fixing apparatus 20 and the frame 10 form a ring-shaped space. The second body and the first body are detachably connected. The main functional unit 30 is detachably mounted on the frame 10. The elastic component 40 includes an initial state and a deformed state, and the elastic component 40 is connected to the main functional unit 30. The elastic component 40 generates an elastic force in the deformed state, and the elastic force is configured to detach the main functional unit 30 from the frame 10. Here, the main functional unit 30 may be a display screen of a smart watch, and is a detachable screen.

In this embodiment of the present application, the elastic component is provided, and the elastic component includes the initial state and the deformed state, and the elastic component is connected to the main functional unit, the elastic component generates an elastic force in the deformed state, and the elastic force is configured to detach the main functional unit from the frame, thus when the main functional unit is a display device, the display device can be detached from the frame conveniently by a single hand.

Third Embodiment of the Electronic Device

The electronic device according to this embodiment of the present application is shown in FIGS. 1 to 4. The electronic device includes a first body and a second body. The first body includes a frame 10 and a fixing apparatus 20, and the second body includes a main functional unit 30 and an elastic component 40. The fixing apparatus 20 is connected to the frame 10, and is configured to fix the electronic device to the wrist of a user. In the case that the electronic device is fixed to the wrist via the fixing apparatus 20, the fixing apparatus 20 and the frame 10 form a ring-shaped space. The second body and the first body are detachably connected. The main functional unit 30 is detachably mounted on the frame 10. The elastic component 40 includes an initial state and a deformed state, and the elastic component 40 is connected to the main functional unit 30. The elastic component 40 generates an elastic force in the deformed state, and the elastic force is configured to detach the main functional unit 30 from the frame 10.

The electronic device further includes a locking-unlocking device 50 which is arranged on a first part of the frame 10 and a second part of the main functional unit 30. In the case that the main functional unit 30 is mounted on the frame 10, the first part of the frame corresponds to the second part of the main functional unit. The locking-unlocking device 50 is configured to maintain a relative positional relationship between the main functional unit 30 and the frame 10 when the main functional unit 30 is mounted on the frame 10, and to release the relative positional relationship between the main functional unit 30 and the frame 10 when the main functional unit 30 is mounted on the frame 10.

Here, the locking-unlocking device 50 may be triggered by a triggering button 60 of the locking-unlocking device to achieve the locking or unlocking function.

Fourth Embodiment of the Electronic Device

The electronic device according to this embodiment of the present application is shown in FIGS. 1 to 4. The electronic device includes a first body and a second body. The first body includes a frame 10 and a fixing apparatus 20, and the second body includes a main functional unit 30 and an elastic component 40. The fixing apparatus 20 is connected to the frame 10, and is configured to fix the electronic device to the wrist of a user. In the case that the electronic device is fixed to the wrist via the fixing apparatus 20, the fixing apparatus 20 and the frame 10 form a ring-shaped space. The second body and the first body are detachably connected. The main functional unit 30 is detachably mounted on the frame 10. The elastic component 40 includes an initial state and a deformed state, and the elastic component 40 is connected to the main functional unit 30. The elastic component 40 generates an elastic force in the deformed state, and the elastic force is configured to detach the main functional unit 30 from the frame 10.

The electronic device further includes a locking-unlocking device 50 which is arranged on a first part of the frame 10 and a second part of the main functional unit 30. In the case that the main functional unit 30 is mounted on the frame 10, the first part of the frame corresponds to the second part of the main functional unit. The locking-unlocking device 50 is configured to maintain a relative positional relationship between the main functional unit 30 and the frame 10 when the main functional unit 30 is mounted on the frame 10, and to release the relative positional relationship between the main functional unit 30 and the frame 10 when the main functional unit 30 is mounted on the frame 10.

It is to be noted that, the elastic force generated by the elastic component 40 in the deformed state is a force generated by the elastic component 40 during changing from the initial state to the deformed state, wherein the main functional unit 30 is fixed to the frame 10 by the locking-unlocking device 50 when the electronic device is worn on the wrist of the user.

Here, the locking-unlocking device 50 may be triggered by a triggering button 60 of the locking-unlocking device to realize the locking or unlocking function.

Fifth Embodiment of the Electronic Device

The electronic device according to this embodiment of the present application is shown in FIGS. 1 to 4. The electronic device includes a first body and a second body. The first body includes a frame 10 and a fixing apparatus 20, and the second body includes a main functional unit 30 and an elastic component 40. The fixing apparatus 20 is connected to the frame 10, and is configured to fix the electronic device to the wrist of a user. In the case that the electronic device is fixed to the wrist via the fixing apparatus 20, the fixing apparatus 20 and the frame 10 form a ring-shaped space. The second body and the first body are detachably connected. The main functional unit 30 is detachably mounted on the frame 10. The elastic component 40 includes an initial state and a deformed state, and the elastic component 40 is connected to the main functional unit 30. The elastic component 40 generates an elastic force in the deformed state, and the elastic force is configured to detach the main functional unit 30 from the frame 10.

The electronic device further includes a locking-unlocking device 50 which is arranged on a first part of the frame 10 and a second part of the main functional unit 30. In the case that the main functional unit 30 is mounted on the frame 10, the first part of the frame corresponds to the second part of the main functional unit. The locking-unlocking device 50 is configured to maintain a relative positional relationship between the main functional unit 30 and the frame 10 when the main functional unit 30 is mounted on the frame 10, and to release the relative positional relationship between the main functional unit 30 and the frame 10 when the main functional unit 30 is mounted on the frame 10.

It is to be noted that, the elastic force generated by the elastic component 40 in the deformed state is a force generated by the elastic component 40 during changing from the initial state to the deformed state, wherein the main functional unit 30 is fixed to the frame 10 by the locking-unlocking device 50 when the electronic device is worn on the wrist of the user. Correspondingly, the elastic force is released when the elastic component 40 converts from the deformed state to the initial state in the case that the locking-unlocking device 50 releases the relative positional relationship between the main functional unit 30 and the frame 10.

Here, the locking-unlocking device 50 may be triggered by a triggering button 60 of the locking-unlocking device to realize the locking or unlocking function.

Sixth Embodiment of the Electronic Device

The electronic device according to this embodiment of the present application is shown in FIGS. 1 to 4. The electronic device includes a first body and a second body. The first body includes a frame 10 and a fixing apparatus 20, and the second body includes a main functional unit 30 and an elastic component 40. The fixing apparatus 20 is connected to the frame 10, and is configured to fix the electronic device to the wrist of a user. In the case that the electronic device is fixed to the wrist via the fixing apparatus 20, the fixing apparatus 20 and the frame 10 form a ring-shaped space. The second body and the first body are detachably connected. The main functional unit 30 is detachably mounted on the frame 10. The elastic component 40 includes an initial state and a deformed state, and the elastic component 40 is connected to the main functional unit 30. The elastic component 40 generates an elastic force in the deformed state, and the elastic force is configured to detach the main functional unit 30 from the frame 10.

The electronic device further includes a locking-unlocking device 50 which is arranged on a first part of the frame 10 and a second part of the main functional unit 30. In the case that the main functional unit 30 is mounted on the frame 10, the first part of the frame corresponds to the second part of the main functional unit. The locking-unlocking device 50 is configured to maintain a relative positional relationship between the main functional unit 30 and the frame 10 when the main functional unit 30 is mounted on the frame 10, and to release the relative positional relationship between the main functional unit 30 and the frame 10 when the main functional unit 30 is mounted on the frame 10.

It is to be noted that, the elastic force generated by the elastic component 40 in the deformed state is a force generated by the elastic component 40 during changing from the initial state to the deformed state, wherein the main functional unit 30 is fixed to the frame 10 by the locking-unlocking device 50 when the electronic device is worn on the wrist of the user. Correspondingly, the elastic force is released when the elastic component 40 converts from the deformed state to the initial state in the case that the locking-unlocking device 50 releases the relative positional relationship between the main functional unit 30 and the frame 10.

The frame 10 includes a through hole 80, and a first part 301 of the main functional unit is inserted into the through hole 80 to mount the main functional unit 30 on the frame 10.

Seventh Embodiment of the Electronic Device

The electronic device according to this embodiment of the present application is shown in FIGS. 1 to 4. The electronic device includes a first body and a second body. The first body includes a frame 10 and a fixing apparatus 20, and the second body includes a main functional unit 30 and an elastic component 40. The fixing apparatus 20 is connected to the frame 10, and is configured to fix the electronic device to the wrist of a user. In the case that the electronic device is fixed to the wrist via the fixing apparatus 20, the fixing apparatus 20 and the frame 10 form a ring-shaped space. The second body and the first body are detachably connected. The main functional unit 30 is detachably mounted on the frame 10. The elastic component 40 includes an initial state and a deformed state, and the elastic component 40 is connected to the main functional unit 30. The elastic component 40 generates an elastic force in the deformed state, and the elastic force is configured to detach the main functional unit 30 from the frame 10.

The electronic device further includes a locking-unlocking device 50 which is arranged on a first part of the frame 10 and a second part of the main functional unit 30. In the case that the main functional unit 30 is mounted on the frame 10, the first part of the frame corresponds to the second part of the main functional unit. The locking-unlocking device 50 is configured to maintain a relative positional relationship between the main functional unit 30 and the frame 10 when the main functional unit 30 is mounted on the frame 10, and to release the relative positional relationship between the main functional unit 30 and the frame 10 when the main functional unit 30 is mounted on the frame 10.

It is to be noted that, the elastic force generated by the elastic component 40 in the deformed state is a force generated by the elastic component 40 during changing from the initial state to the deformed state, wherein the main functional unit 30 is fixed to the frame 10 by the locking-unlocking device 50 when the electronic device is worn on the wrist of the user. Correspondingly, the elastic force is released when the elastic component 40 converts from the deformed state to the initial state in the case that the locking-unlocking device 50 releases the relative positional relationship between the main functional unit 30 and the frame 10.

The frame 10 includes a through hole 80, and a first part 301 of the main functional unit is inserted into the through hole 80 to mount the main functional unit 30 on the frame 10. The elastic component 40 is connected to the first part 301 of the main functional unit, and the first part 301 of the main functional unit is a protrusion on a bottom surface of the main functional unit 30. The through hole 80 can at least accommodate the elastic component 40 in the deformed state.

Eighth Embodiment of the Electronic Device

The electronic device according to this embodiment of the present application is shown in FIGS. 1 to 4. The electronic device includes a first body and a second body. The first body includes a frame 10 and a fixing apparatus 20, and the second body includes a main functional unit 30 and an elastic component 40. The fixing apparatus 20 is connected to the frame 10, and is configured to fix the electronic device to the wrist of a user. In the case that the electronic device is fixed to the wrist via the fixing apparatus 20, the fixing apparatus 20 and the frame 10 form a ring-shaped space. The second body and the first body are detachably connected. The main functional unit 30 is detachably mounted on the frame 10. The elastic component 40 includes an initial state and a deformed state, and the elastic component 40 is connected to the main functional unit 30. The elastic component 40 generates an elastic force in the deformed state, and the elastic force is configured to detach the main functional unit 30 from the frame 10.

The electronic device further includes a locking-unlocking device 50 which is arranged on a first part of the frame 10 and a second part of the main functional unit 30. In the case that the main functional unit 30 is mounted on the frame 10, the first part of the frame corresponds to the second part of the main functional unit. The locking-unlocking device 50 is configured to maintain a relative positional relationship between the main functional unit 30 and the frame 10 when the main functional unit 30 is mounted on the frame 10, and to release the relative positional relationship between the main functional unit 30 and the frame 10 when the main functional unit 30 is mounted on the frame 10.

It is to be noted that, the elastic force generated by the elastic component 40 in the deformed state is a force generated by the elastic component 40 during changing from the initial state to the deformed state, wherein the main functional unit 30 is fixed to the frame 10 by the locking-unlocking device 50 when the electronic device is worn on the wrist of the user. Correspondingly, the elastic force is released when the elastic component 40 converts from the deformed state to the initial state in the case that the locking-unlocking device 50 releases the relative positional relationship between the main functional unit 30 and the frame 10.

The frame 10 includes a through hole 80, and a first part 301 of the main functional unit is inserted into the through hole 80 to mount the main functional unit 30 on the frame 10. The elastic component 40 is connected to the first part 301 of the main functional unit, and the first part 301 of the main functional unit is a protrusion on a bottom surface of the main functional unit 30. The through hole 80 can at least accommodate the elastic component 40 in the deformed state.

The elastic component 40 is embodied as a wedged elastic component which may be pressed by a single hand to release an elastic force for opening an upper cover. The wedged elastic component includes a pressing plate 401, and an elastic body (not shown). The pressing plate 401 is connected to the first part 301 of the main functional unit 30 at a first position 302 via a movable connecting member. The elastic body has a first end fixed to the first part 301 of the main functional unit at a second position which is different from the first position, and a second end fixed on the pressing plate 401 away from a portion of the pressing plate 401 for connecting the movable connecting member. The elastic body may be a spring.

Ninth Embodiment of the Electronic Device

The electronic device according to this embodiment of the present application is shown in FIGS. 1 to 4. The electronic device includes a first body and a second body. The first body includes a frame 10 and a fixing apparatus 20, and the second body includes a main functional unit 30 and an elastic component 40. The fixing apparatus 20 is connected to the frame 10, and is configured to fix the electronic device to the wrist of a user. In the case that the electronic device is fixed to the wrist via the fixing apparatus 20, the fixing apparatus 20 and the frame 10 form a ring-shaped space. The second body and the first body are detachably connected. The main functional unit 30 is detachably mounted on the frame 10. The elastic component 40 includes an initial state and a deformed state, and the elastic component 40 is connected to the main functional unit 30. The elastic component 40 generates an elastic force in the deformed state, and the elastic force is configured to detach the main functional unit 30 from the frame 10.

The electronic device further includes a locking-unlocking device 50 which is arranged on a first part of the frame 10 and a second part of the main functional unit 30. In the case that the main functional unit 30 is mounted on the frame 10, the first part of the frame corresponds to the second part of the main functional unit. The locking-unlocking device 50 is configured to maintain a relative positional relationship between the main functional unit 30 and the frame 10 when the main functional unit 30 is mounted on the frame 10, and to release the relative positional relationship between the main functional unit 30 and the frame 10 when the main functional unit 30 is mounted on the frame 10.

It is to be noted that, the elastic force generated by the elastic component 40 in the deformed state is a force generated by the elastic component 40 during changing from the initial state to the deformed state, wherein the main functional unit 30 is fixed to the frame 10 by the locking-unlocking device 50 when the electronic device is worn on the wrist of the user. Correspondingly, the elastic force is released when the elastic component 40 converts from the deformed state to the initial state in the case that the locking-unlocking device 50 releases the relative positional relationship between the main functional unit 30 and the frame 10.

The frame 10 includes a through hole 80, and a first part 301 of the main functional unit is inserted into the through hole 80 to mount the main functional unit 30 on the frame 10. The locking-unlocking device 50 is arranged on an inner wall of the through hole 80 of the frame 10 and an outer wall of the first portion of the main functional unit.

Tenth Embodiment of the Electronic Device

On the basis of any one of the above first embodiment to fifth embodiment of the electronic device, the main functional unit may also be embodied as a display screen in scenarios of multiple smart bands in addition to the scenarios of one smart watch or smart band. An application scenario in which the main functional unit is a display screen of two smart bands is shown in FIG. 5. A smart band on the left side includes a first display screen 90, and a smart band on the right side includes a second display screen 91, the two smart bands can be detached from each other and can also be connected. In the case that the two smart bands are combined into one piece, the first display screen 90 and the second display screen 91 form an integral display screen 93.

The above application scenarios may be achieved by a physical detachable-combinable structure based on any one of the above first embodiment to the fifth embodiment of the electronic device, and as described hereinafter, they may also be achieved by electric connections such as magnetically electric connection or other detachable-combinable electric connections.

A physical detachable-combinable structure is described as follows. The electronic device includes a first body and a second body. The first body includes a frame and a fixing apparatus, and the second body includes a main functional unit and an elastic component. The fixing apparatus is connected to the frame, and is configured to fix the electronic device to the wrist of a user. In the case that the electronic device is fixed to the wrist via the fixing apparatus, the fixing apparatus and the frame form a ring-shaped space. The second body and the first body are detachably connected. The main functional unit is detachably mounted on the frame. The elastic component includes an initial state and a deformed state, and the elastic component is connected to the main functional unit. The elastic component generates an elastic force in the deformed state, and the elastic force is configured to detach the main functional unit from the frame.

The electronic device further includes a locking-unlocking device which is arranged on a first part of the frame and a second part of the main functional unit. In the case that the main functional unit is mounted on the frame, the first part of the frame corresponds to the second part of the main functional unit. The locking-unlocking device is configured to maintain a relative positional relationship between the main functional unit and the frame when the main functional unit is mounted on the frame, and to release the relative positional relationship between the main functional unit and the frame when the main functional unit is mounted on the frame.

It is to be noted that, the elastic force generated by the elastic component in the deformed state is a force generated by the elastic component during changing from the initial state to the deformed state, wherein the main functional unit is fixed to the frame by the locking-unlocking device when the electronic device is worn on the wrist of the user. Correspondingly, the elastic force is released when the elastic component converts from the deformed state to the initial state in the case that the locking-unlocking device releases the relative positional relationship between the main functional unit and the frame.

Eleventh Embodiment of the Electronic Device

On the basis of the first embodiment to the ninth embodiment of the electronic device, in one of the above embodiments, the main functional unit is a display module, and a display output area of the display module is arranged on a front side of the main functional unit.

Herein, the display module includes a display assembly and a light transmission assembly. The display assembly is configured to display a first image. The light transmission assembly is configured to convert a light path of a first light beam, corresponding to the first image, emitted from the display assembly, to form a second light beam corresponding to a magnified virtual image of the first image. In the case that the main functional unit and the frame are in a combined state, the first image is displayed in a first display area of the display assembly. In the case that the main functional unit and the frame are in a detached state, the first image is displayed in a second display area of the display assembly. The second display area is larger than the first display area, and the second display area includes the first display area.

On the basis of the eleventh embodiment, various embodiments are shown in the following twelfth embodiment to the fourteenth embodiment.

Twelfth Embodiment of the Electronic Device

In the case that the main functional unit and the frame are in a combined state, the main functional unit is fixed to the frame. A display output area of the display module is arranged on a front side of the main functional unit. The display module is configured to output a first image, and the display module includes a display assembly and a light transmission assembly. The display assembly is configured to display the first image. The light transmission assembly is configured to convert a light path of a first light beam, corresponding to the first image, emitted from the display assembly, to form a second light beam corresponding to a magnified virtual image of the first image.

The display module in this embodiment of the present application is embodied as an optical projection system. The display module includes a first part and a second part. The first part of the display module is a light transmission assembly, and the second part of the display module includes a display assembly and a collimating assembly.

The display assembly is configured to display a second content to be displayed, and projects a first light beam in a light beam manner and outputs the first light beam to the collimating assembly. The collimating assembly is configured to process the outputted first light beam projected in the light beam manner, convert the first light beam into a second light beam, and output the second light beam to the light transmission assembly. The light transmission assembly is also referred to as a light-path converting assembly. The light transmission assembly is made of a transparent material. The light transmission assembly is configured to transmit the second light beam in a material that forms the light transmission assembly. The light transmission assembly includes a reflection unit, and the reflection unit is arranged in a specific area in an excess portion. The reflection unit is configured to change the transmission direction of the second light beam in the transparent material, and project the second light beam in a second direction. The specific area, in which the reflection unit is provided, in the light transmission assembly is a second display output area of the display module.

Further, the display assembly in the display module includes a beam splitting unit, and a display unit. The collimating assembly includes a second collimating unit, a first collimating unit and a polarizing beam splitting unit. The light transmission assembly includes a waveguide unit and a reflection unit. Preferably, the display unit further includes a light emitting unit. The collimating assembly processes the outputted first light beam projected in a light beam manner, converts the first light beam into the second light beam, and outputs the second light beam to the light transmission assembly.

The collimating assembly includes a first collimating unit and a second collimating unit arranged opposite to each other, and a polarizing bean splitting unit arranged between the first collimating unit and the second collimating unit. The first light beam outputted by the display assembly is initially reflected by the polarizing beam splitting unit to the first collimating unit, and then is collimated by the first collimating unit and the second collimating unit, and finally is emitted as the second light beam by the polarizing beam splitting unit.

Herein, each of the first collimating unit and the second collimating unit may be a single lens or a lens set designed as desired.

The light transmission assembly is configured to transmit the second light beam in the material which forms the light transmission assembly, and finally outputs the second light beam to a viewer. The light transmission assembly includes a waveguide unit and a reflection unit. By setting the position and angle of the reflection unit, the second light beam may be controlled and guided to be emitted to a specific position. In a first case, the collimating assembly and the display assembly are located on a first side of a plane in which the waveguide unit is located, and under the action of the reflection unit, the second light beam may be emitted to a second side of the plane in which the waveguide unit is located, and the first side and the second side are opposite sides of the plane in which the waveguide unit is located.

In the case that the display module is applied in a smart watch, the above exemplary configuration may be adopted to allow the second light beam to be emitted to the second side, i.e., to allow the second light beam to be emitted to eyes of the user who wears and watches the wrist strip type electronic device. Further, the emitting direction of the display module may be set according to the watching requirement, for example, the rotation of the display unit may be controlled, to control the emitting direction of the reflection unit, to achieve the switching of bidirectional display of the display module. In this embodiment of the present application, the reflection unit may be a single prism or a prism set designed as desired.

In this embodiment of the present application, as shown in FIG. 6, in the case that the main functional unit and the frame are in a combined state, the main functional unit is fixed to the frame, and the display output area of the display module is arranged on a front side of the main functional unit. In the combined state, the output image seen by the viewer (i.e., the user) is actually presented in an effect watching from a long distance, and the first display area is a partial area of the display unit.

Unlike the state shown in FIG. 6, in the case that the main functional unit and the frame are in a detached state, the main functional unit is detached from the frame by the user via an elastic force released by the elastic component. The display output area of the display module is arranged on the front side of the main functional unit. In the detached state, the output image seen by the viewer (i.e., the user) is actually presented in an effect watching from a long distance, and the second display area is a partial area of the display unit.

Concerning the image contents viewed from the first display area and the second display area, the second display area is lager than the first display area, and is different from the first display area, and the image displaying in the second display area is presented in an effect that being magnified by multiple times via a magnifier. In the case that the display module is in a first display mode, the first display area is smaller than the entire display area of the display unit. In the case that the display module is in a second display mode, the second display area is smaller than or equal to the entire display area of the display unit. In this embodiment, the first display area and the second display area are both in a center area of the display unit, i.e., the centers of the first display area and the second display area coincide with the center of the display unit, hence, the second display area includes the first display area.

In this embodiment, the electronic device generates control information, and the control information is configured to display the first image. On the basis of the configuration structure and the display principle of the display module, in this embodiment of the present application, the control information is configured to control the display assembly to emit a first light beam corresponding to the first image, i.e., controlling a display unit in the display assembly to emit a first light beam corresponding to the first image.

Thirteenth Embodiment of the Electronic Device

On the basis of the twelfth embodiment of the electronic device, in the case that the display module is in a first display mode, the display module controls the first display area of the display assembly to display the first image.

In the case that the display module is in a second display mode, the display module controls the second display area of the display assembly to display the first image. The second display area is larger than the first display area, and the second display area includes the first display area.

In this embodiment, the display module controls the first display area of the display assembly to display the first image, or controls the second display area of the display assembly to display the first image, that is, the display module controls the first display area of the display unit of the display assembly to display the first image, or controls the second display area of the display unit of the display assembly to display the first image. In this embodiment, the display unit is a physical device which can project and output a first light beam corresponding to the first image. The display unit has a display area, and the display unit can control the size of the display area according to the working mode of the display module. Preferably, the display area is in a center area of the display unit, i.e., the center of the display area coincides with the center of the display unit. Thus, in this embodiment, in the case that the display module is in the first display mode, the display module controls the first display area of the display assembly to display the first image, i.e., controls the first display area of the display unit to display the first image. In the case that the display module is in the second display mode, the display module controls the second display area of the display assembly to display the first image, i.e., controls the second display area of the display unit to display the first image. The second display area is larger than the first display area, and the second display area includes the first display area.

With the technical solution of this embodiment of the present application, the size of the display area of the first image is adjusted according to the working mode of the display module, which further automatically adjusts the size of the perception picture perceived by the viewer of the electronic device, thereby automatically adjusting the size of the perception picture without requiring the viewer to adjust the viewing distance, and ensuring that the viewer may view the entire display content, and greatly improving the user experience. In addition, the display module can contain more comprehensive and more detailed information. In this way, the electronic device according to this embodiment of the present application can provide information display of larger size and higher resolution without being limited by the size of the electronic device.

Fourteenth Embodiment of the Electronic Device

On the basis of the thirteenth embodiment of the electronic device, in the case that the working mode of the display module of the electronic device is determined according to the distance between the viewer of the electronic device and a visible area of the electronic device, the electronic device controls the display output area of the display assembly of the display module in the electronic device, to change the size of the perception picture which is perceived by the viewer of the electronic device and represents the content of the first image. FIG. 7a is a schematic view of the first display mode; and FIG. 7b is a schematic view of the second display mode. The electronic device being a smart watch is taken as an example, and the display area of the watch face of the smart watch is the visible area. As shown in FIG. 7a, in the case that a distance between a viewer of the electronic device and the visible area is L1 and L1 falls into a first distance range, the interactive manner of the viewer of the electronic device with respect to the electronic device is a first interactive manner. The perception picture perceived by the viewer of the electronic device via the visible area is a first perception picture 601 shown in FIG. 7a. The dash lines between eyes of the viewer and the display area of the watch face of the smart watch indicate the viewing direction of the eyes of the viewer. The transmission direction of the light beam is between the display area of the watch face of the smart watch and the first perception picture. In this embodiment, the content of the first perception image is the first image, and the viewer views the entire content of the first image via the display area of the watch face of the smart watch. As shown in FIG. 7b, in the case that the distance between the viewer of the electronic device and the visible area is L2 and the L2 falls into a second distance range, the interactive manner of the viewer of the electronic device with respect to the electronic device is a second interactive manner. The perception picture perceived by the viewer of the electronic device via the visible area is a second perception picture 602 shown in FIG. 7b. The second size of the second perception picture 602 is larger than the first size of the first perception picture 601, and the contents of the first perception picture 601 and the second perception picture 602 are both the first image. That is, in the case that the viewer of the electronic device interacts with the electronic device in the first interactive manner, the viewer views a relatively small perception picture via the visible area, and the content of the perception picture is the entire content of the first picture; and in the case that the viewer of the electronic device interacts with the electronic device in the second interactive manner, the viewer views a relatively large perception picture via the visible area, and the content of the perception picture is also the entire content of the first picture.

Fifteenth Embodiment of the Electronic Device

On the basis of the above embodiments of the electronic device, the electronic device includes a first body and a second body which are detachably connected. The electronic device may be a smart band or a smart watch, and etc. These electronic devices may be carried by the user to record some data of the user, and may also be used as a clock, a notebook, a mobile communication tool or the like. However, these electronic devices with multiple functions also have large power consumptions, and are required to be charged timely by the user to ensure normal use of various functions of the electronic devices.

Figure 8:
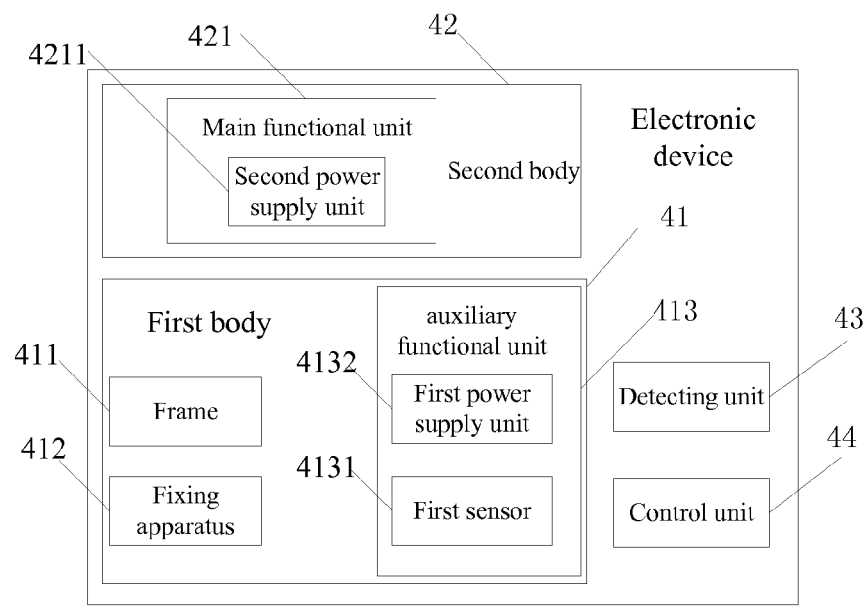
FIG. 8 is a schematic view showing the structure of an embodiment of another electronic device according to the present application.
Figure 9:
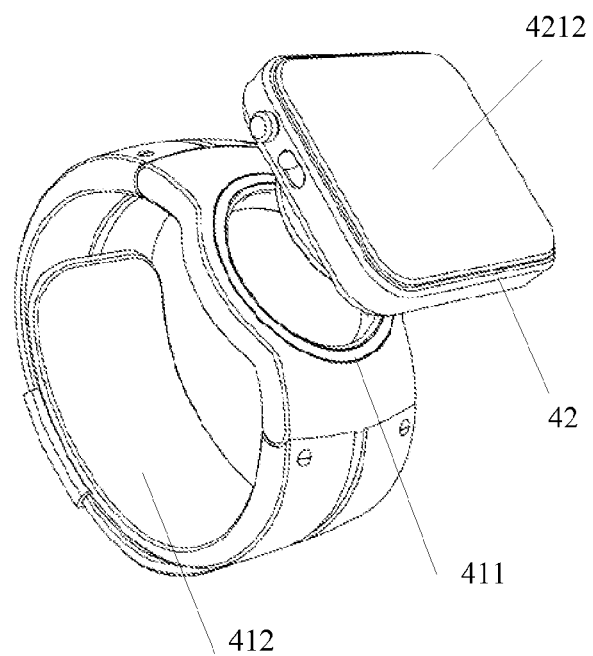
FIG. 9 is a schematic view showing the structure of an embodiment of another electronic device according to the present application.
Figure 10:
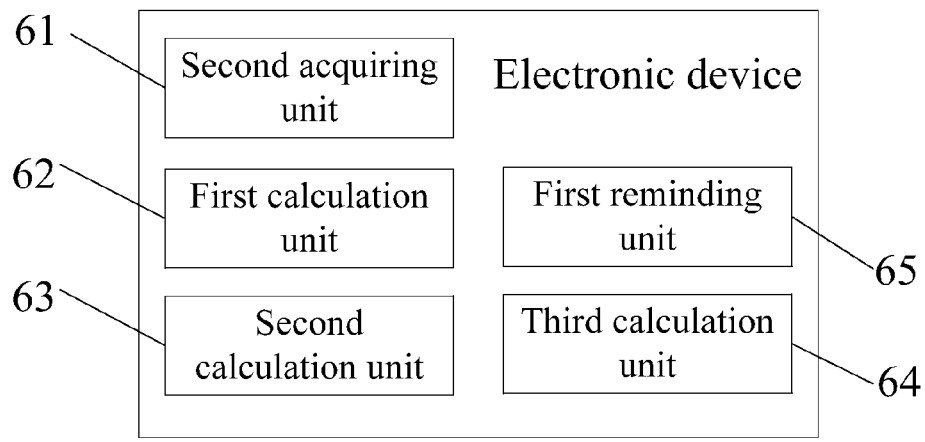
FIG. 10 is a schematic view showing partial structure of the embodiment of another electronic device according to the present application.

In the case that an electronic device, such as a smart band or a smart watch, has insufficient power, the user needs to take off the electronic device for charging, thus, for ensuring that the electronic device can continue to record the data of the user during being charged, an electronic device is further provided according to the present application. The electronic device according to this embodiment is shown in FIGS. 8 to 10. The electronic device includes a first body 41 and a second body 42. The first body 41 includes a frame 411 and a fixing apparatus 412, and the second body 42 includes a main functional unit 421. The fixing apparatus 412 is connected to the frame 411, and is configured to fix the electronic device to an operation body, for example, the wrist of a user. In the case that the electronic device is fixed to the operation body via the fixing apparatus 412, the fixing apparatus 412 and the frame 411 form a ring. The second body 42 and the first body 41 are detachably connected. The main functional unit 421 of the second body 42 is detachably mounted on the frame 411 of the first body 41. Herein, the main functional unit 421 may be a display screen of a smart watch, and is a detachable screen.

The first body 41 further includes an auxiliary functional unit 413, and the auxiliary functional unit 413 includes a first power supply unit 4132. The main functional unit 421 includes a second power supply unit 4211. Hence, in the electronic device according to this embodiment, when the second body 42 is taken off to be charged or for other purposes, the first power supply unit 4132 of the auxiliary functional unit 413 of the first body 41 charges the electronic device to ensure the normal operation of the electronic device.

Therefore, a power supply control method and an electronic device are provided according to the present application, and the method is applied in the electronic device. The electronic device includes a first body and a second body. The first body includes a frame, a fixing apparatus, and an auxiliary functional unit, and the auxiliary functional unit includes a first sensor for real-time detection and a first power supply unit. The second body includes the main functional unit, and the main functional unit includes a second power supply unit. The fixing apparatus is connected to the frame, and is configured to fix the electronic device to the operation body. In the case that the fixing apparatus fixes the electronic device to the operation body, the electronic device forms a ring. The auxiliary functional unit is arranged in the fixing apparatus or the frame, and the auxiliary functional unit is electrically connected to the first power supply unit. The second body and the first body are detachably connected. In practical application, the first body is fixed to the operation body all along, and when it is detected that the second body is detached from the first body, the first power supply unit is controlled to supply power to the auxiliary functional unit; and when it is detected that the second body is coupled to the first body, the second power supply unit of the second body is controlled to supply power to the auxiliary functional unit of the first body and to supply power to the main functional unit of the second body, thereby ensuring that the auxiliary functional unit of the first body is always in the working state and the data of the operation body is recorded in real time, and ensuring the integrity of the data of the operation body recorded by the electronic device.

Sixteenth Embodiment of the Electronic Device

Reference is made to FIG. 8, which is a schematic view showing the structure of an embodiment of an electronic device of the present application. In this embodiment, the electronic device includes a first body 41 and a second body 42. The first body 41 includes a frame 411, a fixing apparatus 412, and an auxiliary functional unit 413. The auxiliary functional unit 413 includes a first sensor 4131 for real-time detection and a first power supply unit 4132. The second body 42 includes the main functional unit 421, and the main functional unit 421 includes a second power supply unit 4211.

The fixing apparatus 412 is connected to the frame 411, and is configured to fix the electronic device to an operation body. In the case that the electronic device is fixed to the operation body via the fixing apparatus 412, the electronic device forms a ring. Thus, in the present application, the electronic device may be fixed to the operation body at the wrist, the neck or the like, via the fixing apparatus 412, and as shown in FIG. 9, the electronic device may be a smart watch.

The auxiliary functional unit 413 is arranged in the fixing apparatus 412 or the frame 411, and the auxiliary functional unit 413 is electrically connected to the first power supply unit 4132. The second body 42 and the first body 41 are detachably connected. The electronic device may further include a detection unit 43 and a control unit 44.

The detection unit 43 is configured to detect whether the second body is detached from the first body, and generate a detection result.

The control unit 44 is configured to control the first power supply unit to supply power to the auxiliary functional unit in the case that the detection result indicates that the second body is detached from the first body; and control the second power supply unit of the second body to supply power to the auxiliary functional unit of the first body and to supply power to the main functional unit of the second body in the case that the detection result indicates that the second body is coupled to the first body.

In the case that the detection result indicates that the second body is coupled to the first body, the control unit 44 is configured to connect the second power supply unit into a first electric circuit in which the auxiliary functional unit is connected, and changing the component property of the first power supply unit from a power supply property to a power consumption property, to allow the second power supply unit connected into the first electric circuit to supply power to the first power supply unit.

Optionally, the first body 41 may further include a power supply interface which is arranged on the frame, and can be connected to an output terminal of the second power supply unit of the second body. The power supply interface may be configured to output a level signal in the case that the second body is coupled to the first body. Therefore, in practical application of this embodiment, the detection unit 43 may determine whether the second body is coupled to the first body by detecting whether a level signal is outputted from the power supply interface.

Apparently, in the present application, the frame or the fixing apparatus may be further provided with an indicator configured to output preset indication information when the second body is coupled to the first body. Therefore, in practical application of this embodiment, the detection unit 43 may determine whether the second body is coupled to the first body by detecting whether preset indication information is outputted by the indicator.

It is to be noted that, in addition to the above manners, other manners may also be adopted in the present application to detect whether the second body is coupled to the first body, which will not be listed herein one by one, and all those manners acquired by the person skilled in the art without making creative efforts should be deemed to fall into the scope of the present application.

According to the above analysis, in practical application of the electronic device according to this embodiment of the present application, in the case that the second body is coupled to the first body, the second power supply unit supplies power to the auxiliary functional unit of the first body and the main functional unit of the second body, and in the case that the second body is detached from the first body, the first power supply unit of the first body supplies power to the auxiliary functional unit, thereby ensuring uninterrupted power supply to the auxiliary functional unit of the first body of the electronic device, to allow the first sensor of the auxiliary functional unit to detect status information of the operation body in real time.

Optionally, on the basis of the above embodiment, the auxiliary functional unit 413 of the first body 41 may further include:
a first acquiring unit configured to acquire first energy storage information of the first power supply unit; and
a first comparison unit configured to compare the first energy storage information with a preset first threshold, and in the case that it is determined that the first energy storage information reaches the first threshold, trigger the control unit 44 to control the second power supply unit to stop supplying power to the first power supply unit and to disconnect the second power supply unit from the first electric circuit of the auxiliary functional unit.

In practical application, when the energy storage information of the first power supply unit reaches the first threshold, it indicates that the first power supply has been fully charged. In this embodiment, when it is determined that the first power supply unit has been fully charged, power supply to the first power supply unit is stopped and the second power supply unit is disconnected from the first electric circuit, thereby protecting the first power supply unit which is fully charged, and avoiding impacting the service life of the first power supply unit due to excessively charging.

Reference is made to FIG. 10, which is a schematic view showing a partial structure of another electronic device according to the present application. On the basis of the above embodiments, the electronic device according to this embodiment may further includes:
a second acquiring unit 61 configured to acquire second energy storage information of the second power supply unit of the second body in the case that the second body is coupled to the first body;
a first calculation unit 62 configured to calculate a first charging duration required by the second power supply unit to reach a fully charged state according to the second energy storage information and third energy storage information corresponding to the fully charged state of the second power supply unit;
a second calculation unit 63 configured to calculate a first power supply duration of the first power supply unit of the first body supplying power to the auxiliary functional unit when the first body is in a fully charged state;
a third calculation unit 64 configured to calculate a first difference value between the first power supply duration and the first charging duration; and
a first reminding unit 65 configured to output first reminding information in the case that the first difference value obtained by the third calculation unit is less than a preset threshold.

The first reminding unit 65 may be an indicator lamp, a buzzer, a speech module, or a displayer and etc., which is not limited in this application.

According to the description of corresponding part of embodiments of the method, in practical application of this embodiment, in the process of the second power supply unit supplying power to the auxiliary functional unit and the main functional unit in the case that the second body is coupled to the first body, if the above duration requirement is met, the first reminding unit outputs the first reminding information, to remind the operation body to detach the second body from the first body, and charge the second power supply unit of the second body, thus when the power of the first power supply unit is entirely consumed, the second power supply unit has been fully charged, thereby ensuring uninterrupted working of the auxiliary functional unit of the first body.

As another embodiment of the present application, taking a smart watch for example, as shown in FIG. 9, the main functional unit 421 of the second body 42 further includes a display screen 4212, and in the case that the second body 42 is coupled to the first body 41, the display screen 4212 is in data connection with the first sensor 4131 of the first body 41, to display the status information of the operation body detected by the first sensor of the first body 41.

It is to be noted that, when the electronic device is in a combined state as shown in FIG. 9, the electronic device is equivalent to a conventional smart watch, which has all the functions of a conventional smart watch, and achieves real-time monitoring of the operation body, and the difference only lies in that the electronic device according to the present application is powered by the second power supply unit of the second body, rather than the first power supply unit of the first body. The functions of the electronic device in the state shown in FIG. 9 may be referred to descriptions of a smart watch in the conventional technology, which will not be described in detail herein.

When the second body of the electronic device is detached from the first body, for facilitating the operation body acquiring a real-time monitoring status of the operation body from the electronic device, the first body 41 may further include an indicator lamp arranged on the frame 411 or the fixing apparatus 412, and the indicator lamp is configured to indicate the working state of the first sensor of the first body and/or the physical state of the operation body detected by the first sensor. Therefore, only when the first body is coupled to the operation body, a current monitoring status of the electronic device may be indicated by flickering of various indicator lamps, thus the operation body may learn the real-time detection information by checking the flickering condition of the indicator lamps, to get a timely treatment when it is determined that the operation body has a bad physical condition.

Therefore, in the electronic device according to the present application, the real-time detection status of the operation body from the electronic device may be indicated or displayed by the display screen of the second body and the indicator lamp of the first body, thereby reminding the operation body timely when the operation body has in a bad physical condition.

A power supply control method is further provided according to the present application, which is applied in an electronic device. The electronic device includes a first body and a second body. The first body includes a frame and a fixing apparatus, and the second body includes a main functional unit. The fixing apparatus is connected to the frame, and is configured to fix the electronic device to an operation body, for example, the wrist of a user. In the case that the electronic device is fixed to the operation body via the fixing apparatus, the fixing apparatus and the frame form a ring. The second body and the first body are detachably connected. The power supply control method according to this embodiment may include:

Step S11: detecting whether the second body is detached from the first body, and generating a detection result.

Since the first body and the second body of the electronic device are detachably connected, for determining the usage mode of the electronic device to determine to the manner for supplying power to the electronic device, the power supply control method according to the present application includes the above step S11, to determine that the first body and the second body are in a combined state or a detached state.

A power supply control method is further provided according to the present application, and is applied in an electronic device. The electronic device includes a first body and a second body detachably connected to the first body, the first body includes a frame, a fixing apparatus, and an auxiliary functional unit having a first power supply unit, the fixing apparatus is connected to the frame and configured to fix the electronic device to an operation body. The fixing apparatus and the frame form a ring-shaped space in the case that the electronic device is fixed to the operation body by the fixing apparatus, the second body includes a main functional unit having a second power supply unit; the method includes:

detecting whether the second body is detached from the first body, and generating a detection result;

controlling the first power supply unit to supply power to the auxiliary functional unit in the case the detection result indicates that the second body is detached from the first body; and controlling the second power supply unit of the second body to supply power to both the auxiliary functional unit of the first body and the main functional unit of the second body in the case that the detection result indicates that the second body is coupled to the first body.

A power supply control method is further provided according to the present application, and is applied in an electronic device. The electronic device includes a first body and a second body. The first body includes a frame, a fixing apparatus, and an auxiliary functional unit, and the auxiliary functional unit includes a first sensor for real-time detection and a first power supply unit. The second body includes the main functional unit, and the main functional unit includes a second power supply unit. The fixing apparatus is connected to the frame, and is configured to fix the electronic device to an operation body. In the case that the fixing apparatus fixes the electronic device to the operation body, the electronic device forms a ring. The auxiliary functional unit is arranged in the fixing apparatus or the frame, and is electrically connected to the first power supply unit. The second body and the first body are detachably connected. In practical application, the first body is fixed to the operation body all along, and when it is detected that the second body is detached from the first body, the first power supply unit is controlled to supply power to the auxiliary functional unit; and when it is detected that the second body is coupled to the first body, the second power supply unit of the second body is controlled to supply power to the auxiliary functional unit of the first body and the main functional unit of the second body, thereby ensuring that the auxiliary functional unit of the first body is in the working condition all along to record the data of the operation body in real time, and ensuring the integrity of the data of the operation body recorded by the electronic device.

Figure 11:
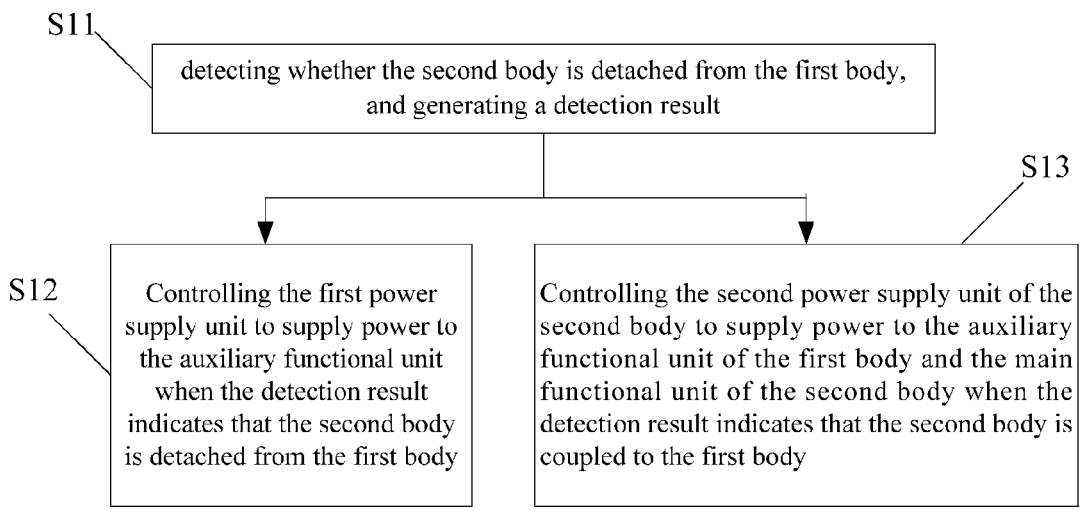
FIG. 11 is a flow chart of an embodiment of a power supply control method according to the present application.

Reference is made to FIG. 11, which is a flow chart of an embodiment of a power supply control method. The power supply control method is applied in an electronic device, and the electronic device may include a first body and a second body. The first body includes a frame, a fixing apparatus, and an auxiliary functional unit, and the auxiliary functional unit includes a first sensor for real-time detection and a first power supply unit. The second body includes the main functional unit, and the main functional unit includes a second power supply unit. The fixing apparatus is connected to the frame, and is configured to fix the electronic device to the operation body. In the case that the fixing apparatus fixes the electronic device to the operation body, the electronic device forms a ring. The auxiliary functional unit is arranged in the fixing apparatus or the frame, and the auxiliary functional unit is electrically connected to the first power supply unit. The second body and the first body are detachably connected. The power supply control method according to this embodiment may include steps S11 to S13.

Step S11 may include detecting whether the second body is detached from the first body, and generating a detection result.

In practical application of this embodiment, for ensuring the electronic device can record the data of the user in real time, the first body of the electronic device has to be fixed to the operation body (i.e., the user) all along, to allow the first sensor of the auxiliary functional unit in the first body to detect the status information of the operation body in real time, for example, information relevant to physical health such as the pulse, the heartbeat, or motion duration and sleeping duration of the operation body, and etc., and the status information is provided to be checked or as reference in the future.

Regarding the power supply to the first body, the first power supply unit included in the first body may supply power to the auxiliary functional unit, or the second power supply unit of the second body may supply power to the auxiliary functional unit of the first body in the case that the second body is coupled to the first body, as long as an uninterrupted power supply to the first body can be ensured.

Optionally, in this embodiment, the frame of the first body may be provided with a power supply interface. The power supply interface is configured to connect with an output terminal of the second power supply unit of the second body and output a level signal in the case that the second body is coupled to the first body. Thus, in practical application of this embodiment, whether the second body is detached from the first body can be determined by detecting whether a level signal is outputted from the power supply interface.

Apparently, in the present application, the frame or the fixing apparatus of the first body may be further provided with a reminding unit configured to output combination reminding information when the second body is coupled to the first body. Therefore, in practical application, whether the second body is coupled to the first body can be determined by detecting whether the combination reminding information is outputted by the reminding unit.

The reminding unit may be an indicator lamp, a buzzer, a speech module and etc., which is not limited in the present application.

It is to be noted that, in addition to the two methods described above, other methods may also be adopted to detect whether the second body is detached from the first body, which will not be listed herein one by one.

Step S12 may include controlling the first power supply unit to supply power to the auxiliary functional unit in the case that the detection result indicates that the second body is detached from the first body.

In practical application, in the case that the second body is detached from the first body, it is required to ensure that the auxiliary functional unit is sustained to work by energy storage of the first power supply unit of the first body, till the second body is coupled to the first body. That is, for ensuring uninterrupted working of the first body of the electronic device, the energy storage of the first power supply unit of the first body is required to satisfy certain conditions in the case that the second body is detached from the first body, for example, the first power supply unit is required to be in a fully charged state.

In a process that the first power supply unit supplies power to the auxiliary functional unit, current energy storage information of the first power supply unit may be detected in real time, and when it is detected that the current energy storage reaches a certain threshold, reminding information reminding that the first power supply unit has insufficient power is outputted to remind the user to couple the second body to the first body.

Optionally, in the process that the first power supply unit supplies power to the auxiliary functional unit, when the reminding information reminding that the first power supply unit has insufficient power is outputted, if the second power supply unit of the second body has been fully charged, the second body may be directly coupled to the first body; and if the second power supply unit of the second body has not been fully discharged, the second body may be coupled to the first body till the reminding information reminding that the first power supply unit has excessively low power is outputted.

Therefore, when the first power supply unit has excessively low power, no matter the second power supply unit of the second body is fully charged or not, for ensuring uninterrupted working of the first body, it is required to couple the second body to the first body, thus the second power supply unit of the second body can supply power to the auxiliary functional unit and the main functional unit.

Step S13 may include controlling the second power supply unit of the second body to supply power to the auxiliary functional unit of the first body and controlling the second power supply unit of the second body to supply power to the main functional unit of the second body in the case that the detection result indicates that the second body is coupled to the first body.

In practical application of this embodiment, once it is determined that the second body is coupled to the first body, the second power supply unit of the second body may supply power to the auxiliary functional unit of the first body and the main functional unit of the second body.

When the detection result indicates that the second body is coupled to the first body, the second power supply unit of the second body is connected into a first electric circuit in which the auxiliary functional unit is connected, to meet the power consumption requirement of the auxiliary functional unit and change the component property of the first power supply unit from a power supply property to a power consumption property, and thus the first power supply unit is changed from a power supply unit to a power consumption module. At this time, the second power supply unit connected into the first electric circuit may supply power to the first power supply unit.

Apparently, it is to be noted that, when it is determined the second body is coupled to the first body, such an implementation is not excluded that the first power supply unit may continue to supply power to the auxiliary functional unit, and when the first power supply unit has insufficient power, the second power supply unit then supplies power to the auxiliary functional unit, and this implementation still falls into the scope of the present application.

On the basis of the above analysis, in this embodiment of the present application, the first body and the second body of the electronic device are detachably connected, the first body includes the first power supply unit, and the second body includes the second power supply unit, thus when the operation body wears the electronic device, if it is reminded that the second power supply unit of the second body has insufficient power, the second body may be directly detached from the first body, and the first power supply unit of the first body may continue to supply power to the first body, thereby ensuring uninterrupted working of the electronic device, and ensuring the integrity of the data of the operation body recorded by the electronic device. Then, when it is reminded that the first power supply unit has insufficient power, the second body having been charged may be coupled to the first body again, and the second power supply unit of the second body supplies power to the auxiliary functional unit of the first body and the main functional unit of the second body again, to make the first power supply unit reach a fully charged state again and at the same time ensuring the normal working of the two functional units, and thus, the first power supply unit can supply power to the auxiliary functional unit in the case that the second body is detached from the first body again. Therefore, the power supply control method applied in the electronic device according to the present application addresses the technical issue that the data of the user recorded by the conventional electronic device is incomplete since the conventional electronic device cannot work normally during being charged.

Figure 12:
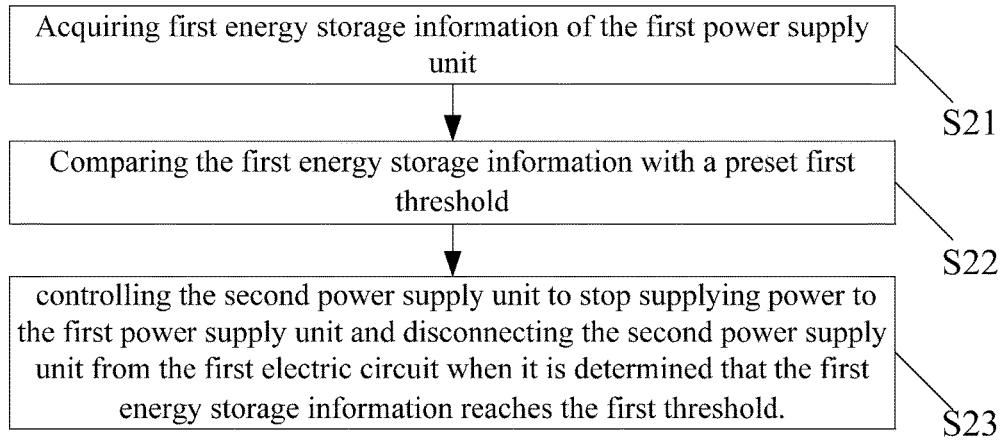
FIG. 12 is a partial flow chart of another embodiment of the power supply control method according to the present application.

It is to be noted that, in practical application of the present application, as long as the second power supply unit is connected into the first electric circuit, in which the auxiliary functional unit is connected, of the first body, the second power supply unit may supply power to the auxiliary functional unit in the first electric circuit all along, and even when the first power supply unit of the auxiliary functional unit has been fully charged, the second power supply unit may still supply power to the first power supply unit. The charging mode that, the second power supply unit always supplies power to the first power supply unit which is fully charged, may inevitably cause waste of energy, and the first power supply unit may also have a reduced service life due to being excessively charged. For addressing this issue, on the basis of the above embodiment and in conjunction with a partial flow chart of another embodiment of the power supply control method according to the present application shown in FIG. 12, the power supply control method according to this embodiment of the present application may further include steps S21 to S23 in the process that the second power supply unit connected in the first electric circuit supplies power to the first power supply unit in the case that the detection result indicates that the second body is coupled to the first body.

Step S21 may include acquiring first energy storage information of the first power supply unit.

The first energy storage information may include current energy storage of the first power supply unit, and may further include a percentage of the current energy storage in a rated energy storage of the first power supply unit (i.e., the energy storage of the first power supply unit in a fully charged state), furthermore, it may further include a charging duration required for the first power supply unit to reach the rated energy storage from the current energy storage.

Step S22 may include comparing the first energy storage information with a first threshold.

The first threshold may be energy storage information corresponding to a fully charged state of the first power supply unit, and may be the rated energy storage of the first power supply unit.

Step S23 may include controlling the second power supply unit to stop supplying power to the first power supply unit and be disconnected from the first electric circuit when it is determined that the first energy storage information reaches the first threshold.

In this embodiment, in the process that the second power supply unit supplies power to the first power supply unit, when it is determined that the first power supply has been fully charged by the second power supply unit, the power supply to the first power supply unit may be stopped and the second power supply unit may be disconnected from the first electric circuit in which the auxiliary functional unit is connected, thereby avoiding the energy waste, and avoiding the impact to the service life of the first power supply unit due to excessive charging.

When it is determined that the first energy storage information of the first power supply unit reaches the first threshold, the reminding information reminding that the first power supply unit has been fully charged may be outputted, and the reminding method of the reminding information is not limited by the present application, and may be performed by an indicator lamp, a speech method, and etc.

Figure 13:
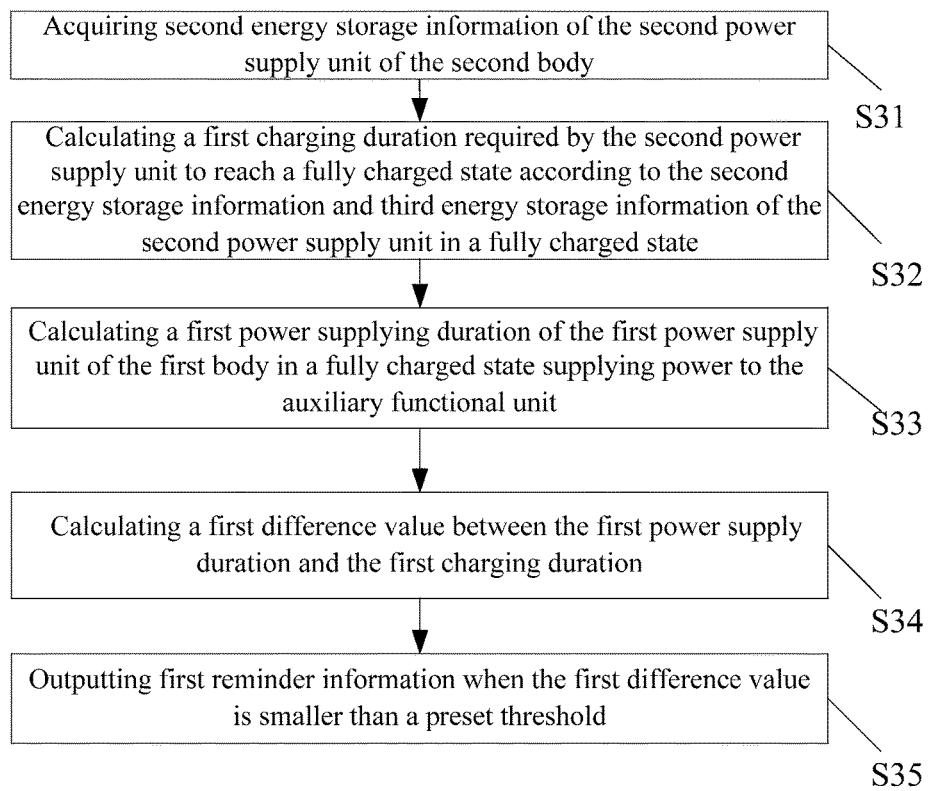
FIG. 13 is a partial flow chart of an embodiment of another power supply control method according to the present application.

Optionally, on the basis of the above embodiments and in conjunction with a partial flowchart of an embodiment of another power supply control method according to the present application as shown in FIG. 13, in the case that the detection result indicates that the second body is coupled to the first body, the power supply control method may further include steps S31 to S35, to further ensure that the first body is coupled to the operation body 24 hours everyday to allow the first sensor of the first body to monitor the operation body in real time.

Step S31 may include acquiring second energy storage information of the second power supply unit of the second body.

According to the above analysis, after the second body has been coupled to the first body, the second power supply unit supplies power to the main functional unit and the auxiliary functional unit, and in this case, the second power supply unit will charge the first power supply unit to allow the first power supply unit to reach a fully discharged state. Meanwhile, the energy storage of the second power supply unit will gradually decrease. In practical application, energy storage information of the second power supply unit may be detected in real time, to allow the second power supply unit to be timely charged once it has insufficient power.

Step S32 may include calculating a first charging duration required by the second power supply unit to reach a fully charged state according to the second energy storage information and third energy storage information corresponding to the fully charged state of the second power supply unit.

In practical application of this embodiment, current energy storage and the rated energy storage of the second power supply unit, and the speed of the charging device charging the second power supply unit may all be acquired, thus in the charging process of the second power supply unit, the first charging duration required for charging the second power supply unit from the current energy storage to the rated energy storage can be calculated in real time based on these known quantities.

Step S33 may include calculating a first power supply duration of the first power supply unit of the first body supplying power to the auxiliary functional unit when the first body is in fully charged state.

In the case that the second body is detached from the first body, the first power supply unit supplies power to the auxiliary functional unit, and in such state, the auxiliary functional unit is the only power consumption module. Power consumption speeds of various members in the auxiliary functional unit are determined, thus, in the case that the rated storage energy and an energy storage margin (i.e., residual energy storage of the first power supply unit that cannot ensure that the normal working of the auxiliary functional unit) of the first power supply unit are known, the first power supply duration, i.e., the maximum power supply duration, of the first power supply unit can be determined according to these known quantities and power consumption speed of the auxiliary functional unit.

Step S34 may include calculating a first difference value between the first power supply duration and the first charging duration.

Step S35 may include outputting first reminding information in the case that the first difference value is less than a preset threshold.

It is to be noted that, in practical application of this embodiment, if the second body is detached from the first body, the auxiliary functional unit of the first body will be powered by the first power supply unit, and the second power supply unit will be charged by a charging device. In this process, for ensuring the first sensor of the first body to uninterruptedly acquire information, it is required that when the electronic device outputs reminding information reminding that the first power supply unit has excessively low power and the first body is about to stop working, the second power supply unit should be fully charged, that is, when the power of the first body has been almost completely consumed, it has to ensure that the second power supply unit is substantially fully charged. That is, it is required that the calculated first charging duration of the second power supply unit should be smaller than the first power supply duration of the first power supply unit.

When it is required to remain a certain safety margin, this embodiment may output the first reminding information reminding that the second power supply unit is required to be charged when the difference value between the first power supply duration and the first charging duration is smaller than a preset threshold, to notify the operation body to charge the second power supply unit timely.

Optionally, on the basis of the above various embodiments, the main functional unit of the second body may further include a display screen. In the case that the second body is coupled to the first body, the display screen may be in data connection with the first sensor of the first body, to display the status information of the operation body detected by the first sensor of the first body.

Taking the electronic device being a smart watch as an example, in a normal condition, i.e., in the case that the second body is coupled to the second body, in addition to the function that the electronic device of the present application is powered by the second power supply unit of the second body, the electronic device also has various functions of a conventional smart watch under a normal condition, for example, timing, displaying, detecting, warning, and etc, which can be referred to the descriptions for the conventional smart watches, and will not be described in detail herein. In addition, in the case that the second body is coupled to the first body, the display screen of the second body of the electronic device is equivalent to a display screen of a conventional smart watch, and has functions of the display screen of the conventional smart watch, such as time displaying, data detecting, and etc. Thus, the operation body may learn his physical condition by checking the content displayed on the display screen, to allow the operation body to get a timely treatment when having a bad physical condition.

Apparently, in practical application of this embodiment, when it is detected that the condition information of the operation body fails to reach a preset standard, a reminder may be given via the display screen, for example, increasing the displaying brightness of the display screen, changing the color of the light of the display screen, and etc, which is not limited in the present application. Furthermore, unlike the display screen of the conventional smart watch, the display screen of the second body of the electronic device according to the present application may further display status information of the energy storage of the first power supply unit of the first body, and the status information of the energy storage of the second power supply unit of the second body.

Optionally, on the basis of the above embodiments, for allowing the electronic device to provide a reminder when the detected status information of the operation body fails to reach the preset standard in the case that the second body is detached from the first body, the frame or the fixing apparatus of the first body in the present application may further be provided with an indicator lamp. The detection of physical condition or other aspects of the operation body by the first sensor of the first body may be indicated by the flickering of the indicator lamp, and when the status information of the operation body detected by the first sensor of the first body fails to reach the preset standard, for example, when it is detected that the heart of the operation body is in abnormal condition, the indicator lamp is controlled to flicker according to a preset requirement, to remind the operation body to get a timely treatment.

According to the above analysis, in practical application of the present application, in the case that the second body is coupled to the first body, the real-time detected content may be displayed by the display screen of the second body. Apparently, herein the indicator lamp of the first body may also indicate the real-time detected condition at the same time. In the case that the second body is detached from the first body, the real-time condition of the operation body detected by the electronic device may be indicated by the indicator lamp of the first body, thereby ensuring that the electronic device in any state can monitor the operation body in real time.

In the case that the second body is coupled to the first body, if the indicator lamp is not activated all along, the above detection result and corresponding reminding content or the like may be displayed by the above display screen.

Therefore, in this embodiment of the present application, by detecting the status information of the operation body in real time, a reminder may be provided by means of the display screen or the indicator lamp or the like when it is detected that the operation body is in a bad physical condition, i.e., the status information of the operation body fails to reach the preset standard, so as to buy an optimum treatment time for the operation body.

In the several embodiments provided by the present application, it should be appreciated that, the method and the device disclosed herein may be implemented in other manners. The embodiments of the device described above are only schematic. For example, the division of the units is only a division on logical function, and there may be other division modes in the practical implementation, for instant, multiple units or components may be combined, or may be integrated into another system; and some features may be omitted or unperformed. In addition, the coupling, direct coupling or communication connection between the components displayed or discussed above may be realized by some interfaces. The indirect coupling or communication connection between the devices or units may be electrical, mechanical or other forms.

The above unit described as a separate component may be or may be not separate physically. The component displayed as a unit may be or may be not a physical unit, that is, may be located at one place or may be distributed on multiple network units. The object of the solution of the embodiment may be achieved by selecting a part or all of the units according to the practical needs.

Furthermore, various function units in the embodiments of the present application may be integrated in one processing unit; or, each of the function units may be a single unit; or two or more function units are integrated in one unit. The above integrated unit may be realized in a form of hardware or in a form of hardware plus software function unit.

It may be appreciated by those skilled in the art that, all of or a part of steps of the above embodiments of the method may be performed by instructing corresponding hardware through a program. The program may be stored in a computer readable storage medium. When being executed, the program performs the steps of the above embodiments of the method. The storage medium includes various medium capable of storing program codes, such as a movable storage device, a Read-Only Memory (ROM), a Random Access Memory (RAM), a magnetic disc or an optical disc.

In the case that the integrated unit is implemented in the form of software functional module and is sold or used as a separate product, it can also be stored in a computer readable storage medium. Based on such understanding, the essence or the part that contributes to the conventional technology of the technical solutions of embodiments of the present application may be expressed in the form of a software product.

The computer software product is stored in a storage medium, and includes several instructions which enables a computer device (which may be a personal computer, a server, or a network device, and etc.) to execute all or part of the method of each embodiment of the present application. The storage medium described above includes various medium capable of storing program codes, such as a movable storage device, a Read-Only Memory (ROM), a Random Access Memory (RAM), a magnetic disc or an optical disc.

The above embodiments are described in a progressive manner. Each of the embodiments is mainly focused on describing its differences from other embodiments, and references may be made among these embodiments with respect to the same or similar portions among these embodiments. For the electronic device disclosed by the embodiments, the description of the electronic device is simple since it corresponds to the method disclosed by the embodiments; and for the related parts, references may be made to the illustration of the method embodiments with respect to the related parts.

It should be noted that the relationship terminologies such as "first", "second" and the like are only used herein to distinguish one entity or operation from another, rather than to necessitate or imply that the actual relationship or order exists between the entities or operations. Furthermore, terms of "include", "comprise" or any other variants are intended to be non-exclusive. Therefore, a process, method, article or device including a plurality of components includes not only the listed components but also include other components that are not enumerated, or also include the components inherent for the process, method, article or device. Without other limitations, the component defined by the statement "comprising (including) one . . . " does not exclude the case that other similar components may exist in the process, method, article or device having the above component.

The above description is only exemplary embodiments of the present application. It should be noted that, for the person skilled in the art, a few of modifications and improvements may be made to the present application without departing from the principle of the present application. The scope of the present application is defined by the claims.

What is claimed is:

1. An electronic device, comprising:
a first body, comprising a frame and a fixing apparatus, the fixing apparatus being connected to the frame and configured to fix the electronic device to an operation body, the fixing apparatus and the frame forming a ring-shaped space in the case that the electronic device being fixed to the operation body by the fixing apparatus; and
a second body detachably connected to the first body, the second body comprising a main functional unit; and
wherein the main functional unit is detachably mounted to the frame; and the second body further comprises an elastic component connected to the main functional unit, the elastic component comprises an initial state and a deformed state, the elastic component is configured to generate an elastic force when in the deformed state to detach the main functional unit from the frame;
wherein the main functional unit is a display module, and a display output area of the display module is arranged on a front side of the main functional unit; and
wherein the display module comprises:
a display assembly configured to display a first image; and
a light transmission assembly configured to convert a light path of a first light beam which is emitted from the display assembly and corresponding to the first image, to form a second light beam corresponding to a magnified virtual image of the first image;
wherein the display assembly comprises a first display area and a second display area, the first display area is configured to display the first image if the main functional unit is mounted to the frame, and the second display area is configured to display the first image if the main functional unit is detached from the frame; the second display area is larger than the first display area, and the second display area comprises the first display area.

2. The electronic device according to claim 1, further comprising:
a locking-unlocking device being arranged on a first part of the frame and a second part of the main functional unit, wherein the first part of the frame corresponds to the second part of the main functional unit in the case that the main functional unit is mounted to the frame;
wherein the locking-unlocking device is configured to maintain or release a relative positional relationship between the main functional unit and the frame.

3. The electronic device according to claim 2, wherein the elastic force is a force generated by the elastic component during changing from the initial state to the deformed state in the case that the main functional unit is fixed to the frame by the locking-unlocking device.

4. The electronic device according to claim 3, wherein the elastic force is released when the elastic component changing from the deformed state to the initial state in the case that the locking-unlocking device releases the relative positional relationship between the main functional unit and the frame.

5. The electronic device according to claim 4, wherein a through hole is defined in the frame; and a first part of the main functional unit is inserted into the through hole to mount the main functional unit to the frame.

6. The electronic device according to claim 5, wherein the elastic component is connected to the first part of the main functional unit; the first part of the main functional unit is a protrusion on a bottom surface of the main functional unit; and the through hole is configured to accommodate at least the elastic component when the elastic component is in the deformed state.

7. The electronic device according to claim 6, wherein the elastic component is a wedged elastic component.

8. The electronic device according to claim 7, wherein the wedged elastic component comprises:
a pressing plate connected to the first part of the main functional unit at a first position via a movable connecting member; and
an elastic body, having a first end fixed to the first part of the main functional unit at a second position which is different from the first position, and a second end fixed on the pressing plate away from a portion of the pressing plate for connecting the movable connecting member.

9. The electronic device according to claim 5, wherein the locking-unlocking device is arranged on an inner wall of the through hole of the frame and an outer wall of the first portion of the main functional unit.

10. The electronic device according to claim 1, wherein the first body further comprises an auxiliary functional unit having a first sensor for real-time detection and a first power supply unit, the auxiliary functional unit is arranged on the fixing apparatus or the frame, and electrically connected to the first power supply unit; the main functional unit comprises a second power supply unit; the electronic device further comprises:
- a detection unit configured to detect whether the second body is detached from the first body, and generate a detection result; and
- a control unit configured to control the first power supply unit to supply power to the auxiliary functional unit in the case that the detection result indicates that the second body is detached from the first body, and control the second power supply unit of the second body to supply power to both the auxiliary functional unit of the first body and the main functional unit of the second body in the case that the detection result indicates that the second body is coupled to the first body.

11. The electronic device according to claim 10, wherein in the case that the detection result indicates that the second body is coupled to the first body, the control unit is configured to connect the second power supply unit with a first electric circuit to which the auxiliary functional unit is connected, and change component property of the first power supply unit, to control the second power supply unit to supply power to the first power supply unit.

12. The electronic device according to claim 11, further comprising:
- a first acquiring unit configured to acquire first energy storage information of the first power supply unit; and
- a first comparison unit configured to compare the first energy storage information with a preset first threshold, and in the case that the first energy storage information reaches the first threshold, trigger the control unit to control the second power supply unit to stop supplying power to the first power supply unit and disconnect the second power supply unit from the first electric circuit to which the auxiliary functional unit is connected.

13. The electronic device according to claim 12, further comprising:
- a second acquiring unit configured to acquire second energy storage information of the second power supply unit in the case that the second body is coupled to the first body;
- a first calculation unit configured to calculate a first charging duration required by the second power supply unit to reach a fully charged state, according to the second energy storage information and third energy storage information corresponding to the fully charged state of the second power supply unit;
- a second calculation unit configured to calculate a first power supply duration of the first power supply unit for supplying power to the auxiliary functional unit when the first power supply unit is in fully charged state;
- a third calculation unit configured to calculate a first difference value between the first power supply duration and the first charging duration; and
- a first reminding unit configured to output first reminding information in the case that the first difference value is less than a preset threshold.

14. The electronic device according to claim 10, wherein the first body further comprises:
- a power supply interface arranged on the frame, the power supply interface is configured to connect with an output terminal of the second power supply unit of the second body and output level signal in the case that the second body is coupled to the first body.

15. The electronic device according to claim 10, wherein the main functional unit of the second body further comprises a display screen, and in the case that the second body is coupled to the first body, the display screen is in data connection with the first sensor of the first body, to display status information of the operation body detected by the first sensor of the first body.

* * * * *